United States Patent [19]

Nakai et al.

[11] Patent Number: 4,638,094
[45] Date of Patent: Jan. 20, 1987

[54] PROCESS FOR PRODUCING PHENYLACETONES

[75] Inventors: Mamoru Nakai; Takuji Enomiya, both of Ube, Japan

[73] Assignee: Ube Industries, Ltd., Ube, Japan

[21] Appl. No.: 518,691

[22] Filed: Jul. 29, 1983

[30] Foreign Application Priority Data

| Aug. 6, 1982 [JP] | Japan | 57-136346 |
| Aug. 10, 1982 [JP] | Japan | 57-138024 |
| Dec. 7, 1982 [JP] | Japan | 57-213324 |
| Jan. 11, 1983 [JP] | Japan | 58-001744 |
| Jan. 13, 1983 [JP] | Japan | 58-002854 |
| May 26, 1983 [JP] | Japan | 58-091474 |
| Jun. 6, 1983 [JP] | Japan | 58-099579 |
| Jun. 9, 1983 [JP] | Japan | 58-101665 |

[51] Int. Cl.⁴ .................................................. C07C 45/00
[52] U.S. Cl. ............................................................ 568/309
[58] Field of Search ............................... 568/309, 401

[56] References Cited

U.S. PATENT DOCUMENTS

| 2,542,985 | 2/1951 | Bond | 568/309 |
| 3,384,669 | 5/1968 | MacLean et al. | 568/401 |
| 3,578,698 | 5/1971 | Hayden | 568/401 |
| 3,671,590 | 6/1972 | Wiese et al. | 568/309 |
| 3,850,990 | 11/1974 | Young | 568/309 |
| 4,481,373 | 11/1984 | Okumura et al. | 568/401 |

FOREIGN PATENT DOCUMENTS

625138  8/1961  Canada .............................. 568/401

OTHER PUBLICATIONS

Lloyd et al., Journ. Org. Chem., vol. 34(12), p. 3949 (1969).

Primary Examiner—Ethel G. Love
Attorney, Agent, or Firm—Finnegan, Henderson, Farabow, Garrett, & Dunner

[57] ABSTRACT

A phenylacetone or its derivative having the general formula (I):

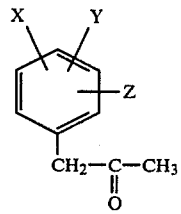

wherein X, Y, and Z are independently a hydrogen atom, a hydroxyl group, a halogen atom, a nitro group, an amino group, a lower alkyl group having 1 to 6 carbon atoms, a lower alkoxy group having 1 to 6 carbon atoms, or a benzyloxy group and any two substituents of X, Y, and Z may form, together with the benzene ring, a heterocycling ring having 5 to 7 members including 1 or 2 oxygen atoms is produced at a high yield and a high selectivity by reacting a 3-phenylpropylene or its derivative having the general formula (II):

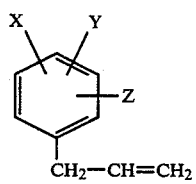

wherein X, Y, and Z are as defined above, with an alkyl nitrite having the general formula (III):

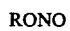

wherein R is an aliphatic, aromatic, or alicyclic saturated or unsaturated hydrocarbon group in the presence of (a) water, (b) an alcohol, (c) a palladium catalyst, and (d) an optional amine or copper compound, or by reacting the above-mentioned 3-phenylpropylene or its derivative with the above-mentioned alkyl nitrite in the presence of (a) an alcohol, (b) a palladium catalyst and (c) an optional amine or copper compound to form 1-phenyl-2,2-dialkoxypropane or it derivative having the general formula (IV):

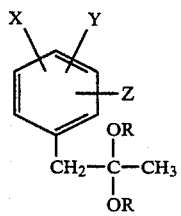

wherein X, Y, Z and R are as defined above, followed by hydrolyzing the reaction product.

16 Claims, No Drawings

PROCESS FOR PRODUCING PHENYLACETONES

BACKGROUND OF THE INVENTION

1. Field of the Invention

The present invention relates to a process for producing a phenylacetone or its derivative.

2. Description of the Prior Art

Phenylacetone and its derivatives ("phenylacetones" hereinbelow) are useful as intermediates for various agricultural chemicals and pharmaceutical preparations. For example, 4-hydroxy-3-methoxyphenylacetone (HMPA), 3,4-dimethoxyphenylacetone (DMPA), and 3,4-methylenedioxyphenylacetone are utilized as intermediates for producing L-alpha-methyldopa, which is used as antihypertensive. Thus, the phenylacetones are practically useful compounds. However, industrially satisfactory processes for producing phenylacetones have not yet been developed.

For instance, British Patent Specification No. 1119612 discloses a process for producing DMPA by reacting 1-(3,4-dimethoxyphenyl)propylene with peroxides such as peracetic acid, followed by treating the resultant diol type products with acidic substances such as zinc chloride. However, this process is not entirely satisfactory in industrial use because the yield of the treatment step with an acidic substance is low and that the special caution should be taken in the handling of the peroxides because of their explosive properties.

Furthermore, the Journal of the American Chemical Society (J.A.C.S.) 77, 700 (1955) discloses a process for producing DMPA by reacting 3,4-dimethoxyphenyl acetonitrile with sodium ethoxide in a solvent such as ethyl acetate to form the acetylated product, followed by hydrolysis. However, this process includes problems that water should be completely removed from the reaction system, which sodium ethoxide is used, in order to prevent hydrolysis of the sodium ethoxide, that the yield of the desired product in the hydrolysis step is low, and that the large number of steps in the entire process is required taking into account the steps necessary to prepare the starting 3,4-dimethoxyphenyl acetonitrile from a readily available chemical raw material.

SUMMARY OF THE INVENTION

Accordingly, an object of the present invention is to eliminate the above-mentioned problems and to provide a process for producing phenylacetones from readily available starting materials at a high yield.

Another object of the present invention is to provide a process for producing phenylacetone at a high reaction rate without using severe reaction conditions.

Other objects and advantages of the present invention will be apparent from the description set forth hereinbelow.

In accordance with the present invention, there is provided a process for producing a phenylacetone or its derivative having the general formula (I):

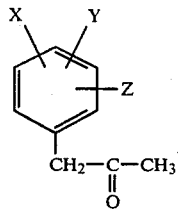

wherein X, Y, and Z are independently a hydrogen atom, a hydroxyl group, a halogen atom, a nitro group, an amino group, a lower alkyl group having 1 to 6 carbon atoms, a lower alkoxy group having 1 to 6 carbon atoms, or a benzyloxy group and any two substituents of X, Y, and Z may form, together with the benzene ring, a heterocyclic ring having 5 to 7 members including 1 or 2 oxygen atoms, comprising the step of reacting 3-phenypropylene or its derivative having the general formula (II):

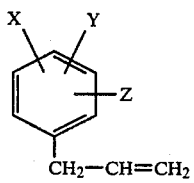

wherein X, Y, and Z are as defined above, with an alkyl nitrite having the general formula (III):

  (III)

wherein R is an aliphatic, aromatic, or alicyclic saturated or unsaturated hydrocarbon group in the presence of (a) water, (b) an alcohol, and (c) a palladium catalyst.

In accordance with the present invention, there is also provided a process for producing phenylacetone or its derivative having the above-mentioned general formula (I) by reacting a 3-phenylpropylene or its derivative having the above-mentioned general formula (II) with an alkyl nitrite having the above-mentioned general formula (III) in the presence of (a) water, (b) an alcohol, (c) a palladium catalyst, and (d) an amine or copper compound.

In accordance with the present invention, there is further provided a process for producing a phenylacetone or its derivative having the above-mentioned general formula (I) by reacting 3-phenylpropylene or its derivative having the above-mentioned general formula (II) with an alkyl nitrite having the above-mentioned general formula (III) in the presence of (a) an alcohol and (b) a palladium catalyst to form 1-phenyl-2,2-dialkoxypropane or it derivative having the general formula (IV):

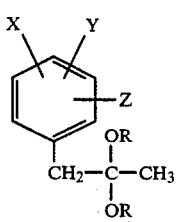

wherein X, Y, Z and R are as defined above and, then, hydrolyzing the reaction product.

In accordance with the present invention, there is still further provided a process for producing phenylacetone or its derivative having the above-mentioned general formula (I) by reacting 3-phenylpropylene or its derivative having the above-mentioned general formula (II) with an alkyl nitrite having the above-mentioned general formula (III) in the presence of (a) an alcohol, (b) a palladium catalyst, and (c) an amine or copper compound and, then, hydrolyzing the reaction product.

DESCRIPTION OF THE PREFERRED EMBODIMENTS

The 3-phenylpropylene and its derivatives ("3-phenylpropylenes" hereinbelow) usable as a starting material in the present invention are those having the general formula (II):

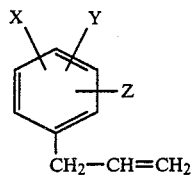

wherein X, Y, and Z are independently a hydrogen atom, a hydroxyl group, a halogen atom, a nitro group, an amino group, a lower alkyl group having 1 to 6 carbon atoms, a lower alkoxy group having 1 to 6 carbon atoms, or a benzyloxy group and any two substituents of X, Y, and Z may form, together with the benzene ring, a heterocyclic ring having 5 to 7 members including 1 or 2 oxygen atoms.

The 3-phenylpropylenes can be readily obtained either by extracting them from natural vegetable oils or by reacting the corresponding benzene or substituted benzene compounds with allyl halides (e.g., $CH_2=CH-CH_2Br$).

The alkyl nitrites usable as another starting material in the present invention are those having the general formula (III):

$$RONO \quad (III)$$

wherein R is an aliphatic, aromatic, or alicyclic saturated or unsaturated hydrocarbon group, desirably an alkyl group having 1 to 10 carbon atoms such as methyl, ethyl, propyl, butyl, pentyl, hexyl, heptyl, octyl, nonyl, and decyl, or a benzyl group. Saturated aliphatic alkyl groups having 1 to 4 carbon atoms such as methyl, ethyl, n-propyl, isopropyl, n-butyl, i-butyl, and sec-butyl are especially desirable as R in the above-mentioned general formula (III).

Although the amount of the alkyl nitrites used in the present reaction may vary over a wide range, the molar ratio of the alkyl nitrites based on 1 mole of the 3-phenylpropylenes is generally 2 moles or more, desirably 2 to 5 moles and more desirably 2.1 to 3.5 moles.

According to the first aspect of the present invention, the 3-phenylpropylene and the alkyl nitrites are reacted in the presence of water, alcohols, and palladium catalyst and, further, optionally amines or copper compounds.

The water is generally introduced into the reaction system in an amount of 1 to 300 moles, desirably 10 to 100 moles, based on 1 mole of the starting 3-phenylpropylenes. The use of a too small amount of the water decreases the yield of the desired phenylacetones. On the other hand, the use of a too large amount of the water does not further improve the reaction and necessitates a troublesome alcohol recovery treatment after the completion of the reaction.

The effects of the alkyl nitrites and water during the reaction are not clearly understood, but it would seem that, without prejudice to the invention, the 3-phenylpropylene and the alkyl nitrites form 1-phenyl-2,2-dialkoxypropanes, which are in turn hydrolyzed with water to form the desired phenylacetones.

The basic reaction of the first aspect of the present invention is as follows:

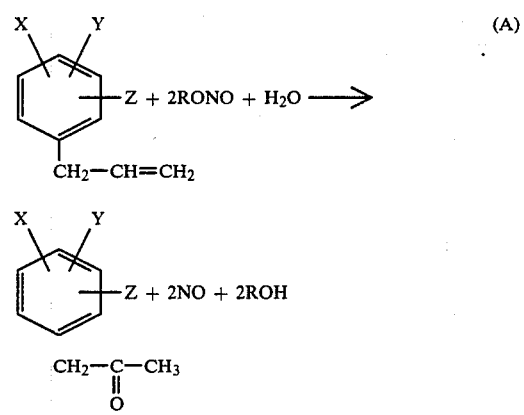

The above-mentioned reaction (A) desirably proceeds in the presence of an alcohol and a palladium catalyst, and optionally, an amine and a copper compound.

Typical examples of the alcohols usable in the present invention are alcohols having 1 to 10 carbon atoms such as methyl alcohol, ethyl alcohol, propyl alcohol, butyl alcohol, pentyl alcohol, hexyl alcohol, heptyl alcohol, octyl alcohol, nonyl alcohol, decyl alcohol, and benzyl alcohol. The alcohols ROH having the same alkyl group R as the alkyl nitrites used in the reaction can be desirably used in the present reaction for the reason that the alcohols contained in the reaction mixture can be readily recovered and reused. The alcohols are desirably used in an amount of 0.5 to 10 liters based on 1 mole of the 3-phenylpropylene used. Hydrous alcohols can be used in the present invention.

The alcohols can also serve as a solvent in the present reaction. However, other inert solvents can be used in the present reaction. Typical examples of the solvents are esters of lower fatty acids such as ethyl acetate and butyl acetate, ethers such as dioxane, dibutyl ether, and tetrahydrofuran, aromatic hydrocarbons such as benzene, toluene and xylene, alicyclic hydrocarbons such as cyclohexane, and aliphatic hydrocarbons such as n-hexane.

The palladium catalysts usable in the present invention include palladium salts and palladium complexes. Typical examples of the palladium salts usable as a catalyst in the present invention are palladium chloride, palladium bromide, palladium iodide, palladium acetate, palladium sulfate, and palladium nitrate, desirably palladium halides such as palladium chloride and palladium bromide. Typical examples of the palladium complexes are dimers of dichloroethylene palladium (II), dimers of dibromoethylene palladium (II), dimers of dichloropropylene palladium (II), bis (acetonitrile) palladium (II) chloride, bis (acetonitrile) palladium (II) bromide, bis (benzonitrile) palladium (II) chloride, bis (benzonitrile) palladium (II) bromide, bis (dimethylsulfoxide) palladium (II) chloride, bis (N,N-dimethylformamide) palladium (II) chloride, bis (N,N'-dimethylacetoamide) palladium (II) chloride, tetrakis (acetonitrile) palladium (II) tetrafluoro borate, tetrakis (acetonitrile) palladium (II) perchlorate, bis (acetylacetonate) palladium (II), sodium tetrachloro palladate (II), lithium tetrabromo palladate (II), lithium bis (oxalato) palladate (II), and sodium tetranitro palladate (II).

The palladium catalysts are desirably used in an amount of 0.001 to 0.2 mole, more desirably 0.005 to 0.1 mole, based on 1 mole of the starting 3-phenylpropylenes. The use of a too small amount of the palladium catalyst does not proceed the desired reaction at a sufficient reaction rate. Contrary to this, the use of a too large amount of the palladium catalyst fails to improve the reaction rate of the desired reaction, the recovery operation of the catalyst becomes troublesome and the loss of the palladium catalyst during the catalyst recovery undesirably increases.

According to the preferred embodiment of the present invention, the production amount of the desired products obtained per unit weight of the palladium catalysts can be further increased in the presence of amines or copper compounds in the reaction system. Thus, the amount of the expensive palladium catalysts to be used can be reduced.

Typical examples of the amines optionally usable as a co-catalyst are those having the general formula (V):

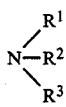
(V)

wherein $R^1$, $R^2$, and $R^3$ are the same or different and represent a hydrogen atom and a lower alkyl group having 1 to 6 carbon atoms and two groups of $R^1$, $R^2$, and $R^3$ may be alkylene groups, which combine together to form a ring.

Typical examples of the amines usable in the present invention are tertiary amines such as trimethylamine, triethylamine, tripropylamine, tributylamine, tripentylamine, and trihexylamine; secondary amines such as dimethylamine, diethylamine, dipropylamine, dibutylamine, dipentylamine, and dihexylamine; primary amines such as methylamine, ethylamine, propylamine, butylamine, pentylamine, and hexylamine; cyclic amines such as piperidine, N-methylpiperidine, N-ethylpiperidine, N-propylpiperidine, N-butylpiperidine, N-pentylpiperidine, N-hexylpiperidine, pyrrolidine, N-methylpyrrolidine, N-ethylpyrrolidine, N-propylpyrrolidine, N-pentylpyrrolidine, and N-hexyopyrrolidine.

These amines can be used in an amount of 0.1 to 2 moles, desirably 0.2 to 1 mole, based on 1 mole of the palladium catalyst. The use of a too small amount of the amines fails to result in the desired co-catalytic effects. Contrary to this, the use of a too large amount of the amines does not result in the further improvement in the desired effects and rather increases the loss of the amines during the recovery thereof.

Typical examples of the copper compounds optionally usable as a co-catalyst in the present invention are copper halides, copper sulfates, copper nitrates, copper hydroxides, and copper oxides. Of these copper compounds, copper halides such as cuprous chloride, cupric chloride, cuprous bromide, and cupric bromide are especially desirable. When the copper compounds other than the copper halides are used, it is desirable to use about 0.1 to 5 moles of a hydrogen halide acid, based on 1 mole of the copper compound, together with the copper compounds.

The copper compounds can be used in an amount of 1 to 30 moles, desirably 3 to 10 moles, based on 1 mole of the palladium catalysts. The use of a too small amount of the copper compounds does not result in the further improvement in the desired effects and rather, complicate the separation and recovery of the catalysts. The most practically desirable combinations of the palladium catalysts and the copper compounds are $PdCl_2$-$CuCl$ and $PdCl_2$-$CuCl_2$ from the standpoint of the availability and economical factor thereof.

The present reaction can be desirably carried out at a temperature of 0° C. to 150° C., desirably 10° C. to 90° C. The use of a too high reaction temperature tends to cause undesirable side reactions such as an isomerization reaction, whereas the use of a too low reaction temperature is not practical because of the low reaction rate. The reaction time is desirably 10 minutes to 5 hours, although this depends upon the reaction conditions. The reaction pressure of the reaction system during the reaction can be an atmospheric pressure to about 200 kg/cm$^2$G, although there is no specific limitation in the reaction pressure.

The present process can be carried out as follows: For example, the starting 3-phenylpropylenes, water, the alcohols, and the palladium catalysts and the optional amines or copper compounds are charged into a reaction vessel. Then, the alkyl nitrites are added to the mixture, causing it to react under the predetermined reaction conditions. It should be noted, however, that the addition order of the reactants and catalysts is not specifically limited.

After completion of the reaction, the resultant NO gas, the unreacted starting materials, water, alcohol, the desired product (i.e., phenylacetones), the optional amines and copper compounds are distilled under a reduced pressure and recovered separately.

The recovered unreacted starting materials and alcohols (which may contain water) and the optional amines and copper compounds can be circulatedly utilized. Furthermore, the NO gas can be used in the production of the alkyl nitrites.

According to the second aspect of the present invention, the 3-phenylpropylene and the alkyl nitrites are reacted in the presence of the alcohols and the palladium catalysts and, further, optionally the amines or copper compounds to form 1-phenyl-2,2-dialkoxypropane or its derivatives as an intermediate, followed by hydrolysis of the reaction product.

The basic reactions of the second aspect of the present invention proceed as follows:

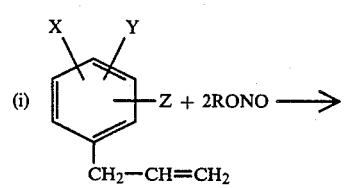

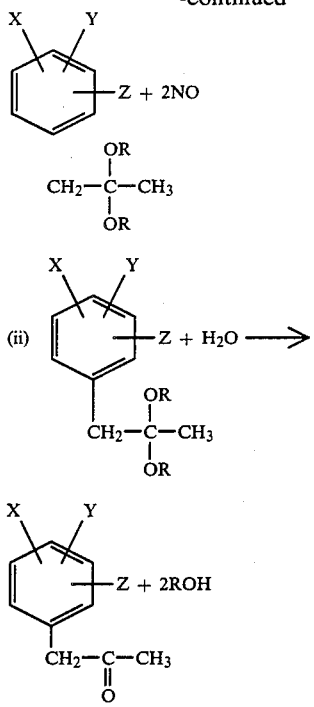

The above-mentioned reaction (B) desirably proceeds in the presence of the above-mentioned alcohols and the above-mentioned palladium catalysts and, optionally, the above-mentioned amines or copper compounds. This reaction can be carried out at a temperature of 0° C. to 150° C., desirably 10° C. to 90° C. optionally in the presence of the above-mentioned inert solvents. The use of a too high reaction temperature tends to cause undesirable side reactions such as an isomerization reaction, whereas the use of a too low temperature is not practical due to the low reaction rate. The pressure within the reaction system during reaction can be an atmospheric pressure to about 200 kg/cm$^2$G. The reaction time is desirably 10 minutes to 5 hours, although this depends upon the reaction conditions.

The present reaction (B) can be carried out as follows: For example, the starting 3-phenylpropylenes, the alcohols, the palladium catalysts and the optional amines or copper compounds are charged into a reaction vessel. The alkyl nitrites are added to the mixture, causing it to react under the predetermined reaction conditions. It should be noted, however, that the addition order of the above-mentioned reactants and catalysts is not specifically limited.

After completion of the reaction, the resultant NO gas, the unreacted starting materials, alcohol, the desired intermediate (i.e., 1-phenyl-2,2-dialkoxypropanes), the optional amines and copper compounds are distilled under a reduced pressure and recovered.

The recovered unreacted starting materials and alcohols as well as the optional amines and copper compounds can be again used. Further, NO gas can be used in the production of the alkyl nitrites.

The 1-phenyl-2,2-dialkoxypropanes thus obtained are hydrolyzed in the presence of water as shown in the above-mentioned reaction (C) either after separating it, or without separating it from the reaction mixture. The amount of water used in the hydrolysis is stoichiometrically 1 mole based on 1 mol of the starting 1-phenyl-2,2-dialkoxypropanes, but is desirably 3 to 500 moles based on 1 mol of the starting 1-phenyl-2,2-dialkoxypropanes. In the case where the amount of the water present in the reaction system is small, the use of solvents other than water is desirable. Even in the case where a large amount of water is used, the use of solvents other than water is also desirable in view of the fact that the starting 1-phenyl-2,2-dialkoxypropanes are not readily soluble in water.

The solvents suitable for use in the hydrolysis of 1-phenyl-2,2-dialkoxypropanes are those which dissolved well both the 1-phenyl-2,2-dialkoxypropanes and the water and also which are substantially inert against the hydrolysis. Typical examples of these solvents are lower alcohols such as methanol, ethanol, propanol, and butanol; ethers such as dioxane and tetrahydrofuran; and carboxylic acids such as acetic acid and propionic acid. Of these examples, the use of methanol, ethanol, propanol, butanol, dioxane, and tetrahydrofuran are particularly desirable. Furthermore, slightly water-soluble alcohols such as pentanol, hexanol, and heptanol can be used as a solvent in combination with dioxane and tetrahydrofuran.

These solvents can be desirably used in an amount of about 0.5 to about 10 liters per 1 mole of 1-phenyl-2,2-dialkoxypropanes.

The hydrolysis can be desirably carried out under a neutral or acidic condition rather than under basic conditions, since the reaction rate of the hydrolysis is low under under basic conditions. Optionally, the pH of the reaction mixture can be adjusted to 4 to 7 by adding a mineral acid such as hydrochloric acid or sulfuric acid. The hydrolysis is generally completed at a temperature of about 0° C. to about 80° C. for about 5 minutes to about 90 minutes. The resultant phenylacetones can be isolated from the reaction mixture by any conventional separation technique such as distillation or extraction.

EXAMPLES

The present invention will now be further illustrated by, but is by no means limited to, the following Examples. In the following examples, the conversion of the starting materials, the yields of the desired intermediates or products, and the Pd turn-over number are calculated as follows:

Conversion of starting material (%) =

$$\frac{\text{Reacted amount (mole) of starting material}}{\text{Charged amount (mole) of starting material}} \times 100$$

Yield of desired intermediates or product (%) =

$$\frac{\text{Formed amount (mole) of desired intermediate or product}}{\text{Charged amount (mole) of starting material}} \times 100$$

Pd turn-over number =

$$\frac{\text{Formed amount (mole) of desired intermediate or product}}{\text{Charged amount (mole) of palladium catalyst}}$$

Example 1

A 0.10 mole amount of the starting 3-phenylpropylene 0.25 mole of methyl nitrite, 0.5 liter of methyl alcohol, 36 g of water, and 0.008 mole (1.42 g) of a palladium chloride catalyst were charged into a reaction vessel. Then, the reaction was carried out at a temperature of 25° C. for 2 hours.

After completion of the reaction, the reaction mixture was gas chromatographically analyzed to quantitatively determine the amounts of the unreacted starting material and the resultant desired product. As a result, the conversion of the starting material was 100% and the yield of the desired product (phenylacetone) was 90%.

Example 2

Phenylacetone was prepared in the same manner as in Example 1, except that n-butyl nitrite and n-butyl alcohol were used in lieu of methyl nitrite and methyl alcohol and that the reaction temperature was changed to 55° C.

After completion of the reaction, the unreacted starting material and the desired product were quantitatively analyzed as in Example 1. The conversion of the starting material was 100% and the yield of the desired product was 87%.

Example 3

4-Hydroxyphenylacetone was prepared in the same manner as in Example 1, except that 3-(4-hydroxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 83%.

Example 4

4-Hydroxyphenylacetone was prepared in the same manner as in Example 2, except that 3-(4-hydroxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 80%.

Example 5

4-Methoxyphenylacetone was prepared in the same manner as in Example 1, except that 3-(4-methoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 95%.

Example 6

4-Methoxyphenylacetone was prepared in the same manner as in Example 2, except that 3-(4-methoxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 90%.

Example 7

4-Hydroxy-3-methoxyphenylacetone was prepared in the same manner as in Example 1, except that 3-(4-hydroxy-3-methoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 85%.

Example 8

4-Hydroxy-3-methoxyphenylacetone was prepared in the same manner as in Example 1, except that ethyl nitrite and ethyl alcohol were used in lieu of methyl nitrite and methyl alcohol, respectively.

After completion of the reaction, the unreacted starting material and the desired product were quantitatively analyzed as in Example 1. The conversion of the starting material was 100% and the yield of the desired product was 82%.

Example 9

4-Hydroxy-3-methoxyphenylacetone was prepared in the same manner as in Example 2, except that 3-(4-hydroxy-3-methoxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 80%.

Example 10

3,4-Dimethoxyphenylacetone was prepared in the same manner as in Example 1, except that 3-(3,4-dimethoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 93%.

Example 11

3,4-Dimethoxyphenylacetone was prepared in the same manner as in Example 8, except that 3-(3,4-dimethoxyphenyl) propylene was used in lieu of 3-phenylpropylene.

After completion of the reaction, the unreacted starting material and the desired product were quantitatively analyzed as in Example 8. The conversion of the starting material was 100% and the yield of the desired product was 91%.

Example 12

3,4-Dimethoxyphenylacetone was prepared in the same manner as in Example 2, except that 3-(3,4-dimethoxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 89%.

Example 13

4-Methoxy-3-nitrophenylacetone was prepared in the same manner as in Example 1, except that 3-(4-methoxy-3-nitrophenyl) propylene was used in lieu of 3-phenylpropylene.

After completion of the reaction, the unreacted starting material and the desired product were quantitatively analyzed as in Example 1. The conversion of the starting material was 100% and the yield of the desired product was 79%.

Example 14

4-Methoxy-3-nitrophenylacetone was prepared in the same manner as in Example 2, except that 3-(4-methoxy-3-nitrophenyl) propylene was used in lieu of 3-phenylpropylene.

After completion of the reaction, the unreacted starting material and the desired product were quantitatively analyzed as in Example 2. The conversion of the starting material was 100% and the yield of the desired product was 76%.

Example 15

3-Amino-4-methoxyphenylacetone was prepared in the same manner as in Example 1, except that 3-(3-amino-4-methoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 83%.

Example 16

3-Amino-4-methoxyphenylacetone was prepared in the same manner as in Example 2, except that 3-(3-amino-4-methoxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 79%.

Example 17

3-Chloro-4-methoxyphenylacetone was prepared in the same manner as in Example 1, except that 3-(3-chloro-4-methoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 85%.

Example 18

3-Chloro-4-methoxyphenylacetone was prepared in the same manner as in Example 2, except that 3-(3-chloro-4-methoxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 82%.

Example 19

3-Bromo-4-ethoxyphenylacetone was prepared in the same manner as in Example 1, except that 3-(3-bromo-4-ethoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 88%.

Example 20

3-Bromo-4-ethoxyphenylacetone was prepared in the same manner as in Example 2, except that 3-(3-bromo-4-ethoxyphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 81%.

Example 21

4-Methoxy-3-methylphenylacetone was prepared in the same manner as in Example 1, except that 3-(4-methoxy-3-methylphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 90%.

Example 22

4-methoxy-3-methylphenylacetone was prepared in the same manner as in Example 2, except that 3-(4-methoxy-3-methylphenyl) propylene was used in lieu of 3-phenylpropylene.

After completion of the reaction, the unreacted starting material and the desired product were quantitatively analyzed as in Example 2. The conversion of the starting material was 100% and the yield of the desired product was 88%.

Example 23

4-Methoxyphenylacetone was prepared in the same manner as in Example 1, except that 3-(4-methoxy)-phenylpropylene and the same amount (0.008 mole) of a palladium bromide were used in lieu of 3-phenylpropylene and the palladium chloride, respectively.

After completion of the reaction, the unreacted starting material and the desired product were quantitatively analyzed as in Example 1. The conversion of the starting material was 100% and the yield of the desired product was 96%.

Example 24

3,4-Methylenedioxyphenylacetone was prepared in the same manner as in Example 1, except that 3-(3,4-methylenedioxyphenyl) propylene and the same amount (0.008 mole) of palladium bromide were used in lieu of 3-phenylpropylene and the palladium chloride, respectively.

After completion of the reaction, the unreacted starting material and the desired product were quantitatively analyzed as in Example 1. The conversion of the starting material was 100% and the yield of the desired product was 95%.

Example 25

2-Hydroxyphenylacetone was prepared in the same manner as in Example 1, except that 3-(2-hydroxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 85%.

Example 26

2-Methoxyphenylacetone was prepared in the same manner as in Example 1, except that 3-(2-methoxyphenyl) propylene was used in lieu of 3-phenylpropylene.

After completion of the reaction, the unreacted starting material and the desired product were quantitatively analyzed as in Example 1. The conversion of the starting material was 100% and the yield of the desired product was 93%.

Examples 27 to 29

A 0.10 mole amount of the starting 3-(4-hydroxy-3-methoxyphenyl) propylene, 0.25 mole of methyl nitrite, 0.5 liter of methyl alcohol, 36 g of water, and 0.008 mole of a catalyst were charged into a reaction vessel. The reaction was carried out at a temperature of 25° C. for 2 hours.

After completion of the reaction, the unreacted starting material and the desired product (4-hydroxy-3-methoxyphenylacetone) were quantitatively analyzed in the same manner as in Example 1.

The results are shown in Table 1.

TABLE 1

| Example No. | Catalyst | Conversion of Starting Material | Yield of Desired Product |
| --- | --- | --- | --- |
| 27 | Palladium bromide | 100% | 92% |
| 28 | Palladium acetate | 55% | 22% |
| 29 | Palladium nitrate | 70% | 30% |

Examples 30 to 32

A 0.10 mole amount of the starting 3-(3,4-dimethoxyphenyl) propylene, 0.25 mole of methyl nitrite, 0.5 liter of methyl alcohol, 36 g of water, and 0.008 mole of a catalyst were charged into a reaction vessel. The reaction was carried out at a temperature of 25° C. for 2 hours.

After completion of the reaction, the unreacted starting material and the desired product (3,4-dimethoxyphenylacetone) were quantitatively analyzed in the same manner as in Example 1.

The results are shown in Table 2.

TABLE 2

| Example No. | Catalyst | Conversion of Starting Material | Yield of Desired Product |
| --- | --- | --- | --- |
| 30 | Palladium bromide | 100% | 96% |
| 31 | Palladium acetate | 66% | 28% |
| 32 | Palladium nitrate | 71% | 34% |

Examples 33 and 34

A 0.10 mole amount of the starting 3-(3-chloro-4-methoxyphenyl) propylene, 0.25 mole of methyl nitrite, 0.5 liter of methyl alcohol, 36 g of water, and 0.008 mole of a catalyst were charged into a reaction vessel. The reaction was carried out at a temperature of 25° C. for 2 hours.

After completion of the reaction, the unreacted starting material and the desired product (3-chloro-4-methoxyphenylacetone) were quantitatively analyzed in the same manner as in Example 1.

The results are shown in Table 3.

TABLE 3

| Example No. | Catalyst | Conversion of Starting Material | Yield of Desired Product |
| --- | --- | --- | --- |
| 33 | Palladium bromide | 100% | 90% |
| 34 | Palladium sulfate | 52% | 21% |

Examples 35 and 36

A 0.10 mole amount of the starting 3-(4-methoxy-3-nitrophenyl) propylene, 0.25 mole of methyl nitrite, 0.5 liter of methyl alcohol, 36 g of water, and 0.008 mole of a catalyst were charged into a reaction vessel. The reaction was carried out at a temperature of 25° C. for 2 hours.

After completion of the reaction, the unreacted starting material and the desired product (4-methoxy-3-nitrophenylacetone) were quantitatively analyzed in the same manner as in Example 1.

The results are shown in Table 4.

TABLE 4

| Example No. | Catalyst | Conversion of Starting Material | Yield of Desired Product |
| --- | --- | --- | --- |
| 35 | Palladium bromide | 100% | 83% |
| 36 | Palladium nitrate | 62% | 33% |

Examples 37 and 38

A 0.10 mole amount of the starting 3-(3-amino-4-ethoxyphenyl) propylene, 0.25 mole of methyl nitrite, 0.5 liter of methyl alcohol, 36 g of water, and 0.008 mole of a catalyst were charged into a reaction vessel. The reaction was carried out at a temperature of 25° C. for 2 hours.

After completion of the reaction, the unreacted starting material and the desired product (3-amino-4-ethoxyphenylacetone) were quantitatively analyzed in the same manner as in Example 1.

The results are shown in Table 5.

TABLE 5

| Example No. | Catalyst | Conversion of Starting Material | Yield of Desired Product |
| --- | --- | --- | --- |
| 37 | Palladium bromide | 100% | 86% |
| 38 | Palladium nitrate | 63% | 33% |

Example 39

A 0.10 mole amount of the starting 3-phenylpropylene, 0.25 mole of methyl nitrite, 0.5 liter of methyl alcohol, 36 g of water, 0.00025 mole of trimethylamine, and 0.0005 mole of a palladium chloride catalyst were charged into a reaction vessel. Then, the reaction was carried out at a temperature of 20° C. for 1.5 hours.

After completion of the reaction, the reaction mixture was gas chromatographically analyzed to quantitatively determine the amounts of the unreacted starting material and the resultant desired product. As a result, the conversion of the starting material was 92%, the yield of the desired product (phenylacetone) was 80%, and the Pd turn-over number was 160.

Example 40

A 0.10 mole amount of the starting 3-(3,4-dimethoxyphenyl) propylene, 0.25 mole of methyl nitrite, 0.5 liter of methyl alcohol, 36 g of water, 0.00025 mole of triethylamine, and 0.0005 mole of a palladium chloride catalyst were charged into a reaction vessel. The reaction was carried out at a temperature of 20° C. for 1.5 hours.

After completion of the reaction, the unreacted starting material and the desired product (3,4-dimethoxyphenylacetone) were quantitatively analyzed and the Pd turn-over number was calculated in the same manner as in Example 39.

The results are shown in Table 6.

Example 41 to 49

Example 40 was repeated, except that 0.00025 mole of each of various amines listed in Table 6 was used in lieu of triethylamine.

The results are shown in Table 6.

TABLE 6

| Example No. | Amines | of Starting Material (%) | Desired Product (%) | Turn-over Number |
|---|---|---|---|---|
| 40 | Triethylamine | 93 | 86 | 172 |
| 41 | Trimethylamine | 94 | 85 | 170 |
| 42 | Tripropylamine | 91 | 82 | 164 |
| 43 | Tributylamine | 88 | 78 | 156 |
| 44 | Dimethylamine | 92 | 83 | 166 |
| 45 | Diethylamine | 92 | 83 | 166 |
| 46 | Dipropylamine | 90 | 81 | 162 |
| 47 | Methylamine | 92 | 81 | 162 |
| 48 | Ethylamine | 92 | 82 | 164 |
| 49 | Propylamine | 90 | 79 | 158 |

*1: Starting material: 3-(3,4-dimethoxyphenyl) propylene
*2: Desired product: 3,4-dimethoxyphenylacetone

Example 50

4-Hydroxy-3-methoxyphenylacetone was prepared in the same manner as in Example 39, except that 3-(4-hydroxy-3-methoxyphenyl) propylene was used in lieu of 3-phenylpropylene.

After completion of the reaction, the unreacted starting material and the desired product were quantitatively analyzed as in Example 39. The conversion of the starting material was 86%, the yield of the desired product was 73%, and the Pd turn-over number was 146.

Example 51

3,4-Methylenedioxyphenylacetone was prepared in the same manner as in Example 39, except that 3-(3,4-methylenedioxyphenyl) propylene was used in lieu of 3-phenylpropylene.

After completion of the reaction, the unreacted starting material and the desired product were quantitatively analyzed as in Example 39. The conversion of the starting material was 92%, the yield of the desired product was 83%, and the Pd turn-over number was 166.

Examples 52 to 58

Example 40 was repeated, except that 0.10 mole of each of various 3-phenylpropylenes listed in Table 7 was used in lieu of 3-(3,4-dimethoxyphenyl) propylene.

The results are shown in Table 7.

TABLE 7

| | Starting 3-phenylpropylenes | | Desired phenylacetones | | |
|---|---|---|---|---|---|
| Example No. | Name | Conversion (%) | Name | Yield (%) | Pd turn-over Number |
| 52 | 3-(4-hydroxyphenyl) propylene | 89 | 4-hydroxyphenylacetone | 78 | 156 |
| 53 | 3-(4-methoxyphenyl) propylene | 93 | 4-methoxyphenylacetone | 82 | 164 |
| 54 | 3-(4-hydroxy-3-methoxyphenyl) propylene | 88 | 4-hydroxy-3-methoxyphenyl-acetone | 77 | 154 |
| 55 | 3-(3,4-methylenedioxy-diphenyl) propylene | 93 | 3,4-methylenedioxyphenyl-acetone | 83 | 166 |
| 56 | 3-(3-benzyloxy-4-methoxyphenyl) propylene | 90 | 3-benzyloxy-4-methoxy-phenylacetone | 80 | 160 |
| 57 | 3-(4-benzyloxy-3-methoxyphenyl) propylene | 87 | 4-benzyloxy-3-methoxy-phenylacetone | 76 | 152 |
| 58 | 3-(4-ethylphenyl) propylene | 92 | 4-ethylphenylacetone | 81 | 162 |

Examples 59 to 61

Example 39 was repeated, except that 0.10 mole of each of various 3-phenylpropylenes listed in Table 8, 0.00025 mole of each of various amines listed in Table 8, and 0.0005 mole of palladium bromide were used in lieu of the palladium chloride.

The results are shown in Table 8.

TABLE 8

| | | Starting 3-phenyl-propylenes | | Desired phenylacetones | | |
|---|---|---|---|---|---|---|
| Example No. | Amines | Name | Conversion (%) | Name | Yield (%) | Pd turn-over number |
| 59 | piperidine | 3-(3,4-dimethoxy-phenyl) propylene | 95 | 3,4-dimethoxy-phenylacetone | 86 | 172 |
| 60 | N—methyl piperidine | 3-(3,4-methylene-dioxyphenyl) propylene | 95 | 3,4-methylene-dioxyphenyl-acetone | 85 | 170 |
| 61 | pyrolidine | 3-(4-hydroxy-3-methoxyphenyl) propylene | 90 | 4-hydroxy-3-methoxyphenyl-acetone | 78 | 156 |

Examples 62 to 64

A 0.10 mole amount of each of various 3-phenylpropylenes listed in Table 9, 0.25 mole of n-butyl nitrite, 0.5 liter of n-butyl alcohol, 36 g of water, 0.00025 mole of triethylamine, and 0.0005 mole of palladium chloride were charged into a reaction vessel. The reaction was carried out at a temperature of 60° C. for 1.5 hours.

After completion of the reaction, the unreacted starting material and the desired phenylacetones were quantitatively analyzed and the Pd turn-over numbers were calculated in the same manner as in Example 39.

The results are shown in Table 9.

TABLE 9

| Example No. | Starting 3-phenylpropylenes | | Desired phenylacetones | | |
|---|---|---|---|---|---|
| | Name | Conversion (%) | Name | Yield (%) | Pd turn-over number |
| 62 | 3-(3,4-methylene-dioxyphenyl) propylene | 69 | 3,4-methylene-dioxyphenylacetone | 58 | 116 |
| 63 | 3-(3,4-dimethoxy-phenyl) propylene | 76 | 3,4-dimethoxy-phenylacetone | 65 | 130 |
| 64 | 3-(4-hydroxy-3-methoxyphenyl) propylene | 65 | 4-hydroxy-3-methoxyphenyl-acetone | 53 | 106 |

Example 65

A 0.10 mole amount of the starting 3-(3,4-dimethoxyphenyl) propylene, 0.25 mole of methyl nitrite, 0.5 liter of methyl alcohol, 36 g of water, and 0.003 mole (corresponding to 0.006 mole of palladium atom) of the dimer of dichloroethylene palladium (II) catalyst were charged into a reaction vessel. Then, the reaction was carried out at a temperature of 20° C. for 1.5 hours.

After completion of the reaction, the reaction mixture was gas chromatographically analyzed to quantitatively determine the amounts of the unreacted starting material and the resultant desired product. As a result, the conversion of the starting material was 100% and the yield of the desired product (3,4-dimethoxyphenylacetone) was 90%.

Example 66

3,4-Dimethoxyphenylacetone was prepared in the same manner as in Example 65, except that 0.006 mole of bis (acetonitrile) palladium (II) chloride was used as a catalyst.

After completion of the reaction, the unreacted starting material and the desired product were quantitatively analyzed as in Example 65. The conversion of the starting material was 100% and the yield of the desired product was 89%.

Example 67

4-Hydroxy-3-methoxyphenylacetone was prepared in the same manner as in Example 65, except that 0.10 mole of 3-(4-hydroxy-3-methoxyphenyl) propylene was used as a starting material and 0.006 mole of bis (acetonitrile) palladium (II) chloride was used as a catalyst.

After completion of the reaction, the unreacted starting material and the desired product were quantitatively analyzed as in Example 65. The conversion of the starting material was 100% and the yield of the desired product was 82%.

Example 68

3,4-Methylenedioxyphenylacetone was prepared in the same manner as in Example 65, except that 0.10 mole of 3-(3,4-methylenedioxyphenyl) propylene was used as a starting material and 0.006 mole of bis (benzonitrile) palladium (II) chloride was used as a catalyst.

After completion of the reaction, the unreacted starting material and the desired product were quantitatively analyzed as in Example 65. The conversion of the starting material was 100% and the yield of the desired product was 88%.

Example 69

3,4-Dimethoxyphenylacetone was prepared in the same manner as in Example 65, except that 0.25 mole of n-butyl nitrite in lieu of methyl nitrite, 0.5 liter of n-butyl alcohol in lieu of methyl alcohol were used and the reaction temperature was changed to 60° C.

After completion of the reaction, the unreacted starting material and the desired product were quantitatively analyzed as in Example 65. The conversion of the starting material was 100% and the yield of the desired product was 83%.

Example 70

A 0.10 mole amount of the starting 3-phenylpropylene, 0.25 mole of methyl nitrite, 0.5 liter of methyl alcohol, 36 g of water, 0.0005 mole of a palladium chloride catalyst, and 0.0025 mole of cuprous chloride were charged were charged into a reaction vessel. Then, the reaction was carried out at a temperature of 20° C. for 1.5 hours.

After completion of the reaction, the reaction mixture was gas chromatographically analyzed to quantitatively determine the amounts of the unreacted starting material and the resultant desired product. As a result, the conversion of the starting material was 94%, the yield of the desired product was 83%, and the Pd turn-over number was 166.

Examples 71 to 76

The reaction of Example 70 was repeated, except that 0.10 mole of each of various 3-phenylpropylenes listed in Table 10 was used as a starting material and 0.0025 mole of $CuCl_2$ or CuCl was used as a copper compound.

The results are shown in Table 10.

TABLE 10

| Example No. | Starting 3-phenylpropylenes | | | Desired phenylacetones | | |
|---|---|---|---|---|---|---|
| | Name | Conversion (%) | Copper compound | Name | Yield (%) | Pd turn-over number |
| 71 | 3-(4-hydroxy-3-methoxyphenyl) propylene | 92 | $CuCl_2$ | 4-hydroxy-3-methoxyphenyl-acetone | 82 | 164 |
| 72 | | 93 | CuCl | | 82 | 164 |
| 73 | 3-(3,4-dimethoxy- | 96 | $CuCl_2$ | 3,4-dimethoxy- | 86 | 172 |

TABLE 10-continued

| Example No. | Starting 3-phenylpropylenes Name | Conversion (%) | Copper compound | Desired phenylacetones Name | Yield (%) | Pd turn-over number |
|---|---|---|---|---|---|---|
| 74 | phenyl) propylene | 95 | CuCl | phenylacetone | 85 | 170 |
| 75 | 3-(3,4-methylene-dioxyphenyl) propylene | 93 | CuCl$_2$ | 3,4-methylene-dioxyphenyl-acetone | 84 | 168 |
| 76 | | 93 | CuCl | | 85 | 170 |

Examples 77 to 79

A 0.10 mole amount of the starting 3-phenylpropylene listed in Table 11, 0.25 mole of n-butyl nitrite, 0.5 liter of n-butyl alcohol, 36 g of water, 0.0025 mole of CuCl$_2$ as a copper compound and 0.0005 mole of a palladium chloride catalyst were charged into a reaction vessel. The reaction was carried out at a temperature of 60° C. for 1.5 hours.

After completion of the reaction, the unreacted starting material and the desired product were quantitatively analyzed and the Pd turn-over number was calculated in the same manner as in Example 70.

The results are shown in Table 11.

TABLE 11

| Example No. | Starting 3-phenylpropylenes Name | Conversion (%) | Desired phenylacetones Name | Yield (%) | Pd turn-over number |
|---|---|---|---|---|---|
| 77 | 3-(4-hydroxy-3-methoxyphenyl) propylene | 63 | 4-hydroxy-3-methoxyphenyl-acetone | 52 | 104 |
| 78 | 3-(3,4-dimethoxyphenyl) propylene | 72 | 3,4-dimethoxy-phenylacetone | 63 | 126 |
| 79 | 3-(3,4-methylene-dioxyphenyl) propylene | 65 | 3,4-methylene-dioxyphenyl-acetone | 56 | 112 |

Examples 80 to 85

A 0.10 mole amount of the starting 3-phenylpropylenes listed in Table 12, 0.25 mole of methyl nitrite, 0.5 liter of methyl alcohol, 36 g of water, 0.0005 mole of a palladium chloride catalyst, and 0.0025 mole of cupric chloride were charged into a reaction vessel. The reaction was carried out at a temperature of 20° C. for 1.5 hours.

After completion of the reaction, the unreacted starting material and the desired product were quantitatively analyzed and the Pd turn-over number was calculated in the same manner as in Example 70.

The results are shown in Table 12.

Example 86

A 0.10 mole amount of the starting 3-(4-hydroxyphenyl) propylene, 0.25 mole of methyl nitrite, 0.5 liter of methyl alcohol, and 0.006 mole of a palladium chloride catalyst were charged into a reaction vessel. Then, the reaction was carried out at a temperature of 20° C. for 1.5 hours.

After the completion of the reaction, the reaction mixture was gas chromatographically analyzed to quantitatively determine the unreacted starting material and the resultant intermediate product (1-(4-hydroxyphenyl)-2,2-dimethoxypropane). As a result, the conversion of the starting material was 100% and the yield of the intermediate product was 85%.

The reaction mixture (containing the intermediate product) obtained above was hydrolyzed at a temperature of 20° C. for 60 minutes by adding 36 g of water.

After completion of the hydrolysis, the desired 4-hydroxyphenylacetone was quantitatively determined by a gas chromatographical analysis. The yield of the desired product was 84%.

Example 87

The reaction of Example 86 was repeated, except that 3-(4-hydroxy-3-methoxyphenyl) propylene was used in lieu of 3-(4-hydroxyphenyl) propylene.

As a result, the conversion of the starting material was 100%, the yield of the intermediate 1-(4-hydroxy-3-methoxyphenyl)-2,2-dimethoxypropane was 85%, and

TABLE 12

| Example No. | Starting 3-phenylpropylenes Name | Conversion (%) | Desired phenylacetones Name | Yield (%) | Pd turn-over number |
|---|---|---|---|---|---|
| 80 | 3-(4-hydroxy-phenyl) propylene | 94 | 4-hydroxyphenyl-acetone | 85 | 170 |
| 81 | 3-(2-methoxy-phenyl) propylene | 96 | 2-methoxyphenyl-acetone | 87 | 174 |
| 82 | 3-(4-methyl-phenyl) propylene | 93 | 4-methylphenyl-acetone | 81 | 162 |
| 83 | 3-(4-nitrophenyl) propylene | 95 | 4-nitrophenyl-acetone | 82 | 164 |
| 84 | 3-(4-chlorophenyl) propylene | 92 | 4-chlorophenyl-acetone | 80 | 160 |
| 85 | 3-(4-benzyloxy-phenyl) propylene | 92 | 4-benzyloxy-phenylacetone | 83 | 166 | the yield of the desired 4-hydroxy-3-methoxyphenylacetone was 84%.

Example 88

The reaction of Example 86 was repeated, except that 3-(3,4-dimethoxyphenyl) propylene was used in lieu of 3-(4-hydroxyphenyl) propylene.

As a result, the conversion of the starting material was 100%, the yield of the intermediate 1-(3,4-dimethoxyphenyl)-2,2-dimethoxypropane was 93%, and the yield of the desired 3,4-dimethoxyphenylacetone was 92%.

Example 89

The reaction of Example 86 was repeated, except that 3-phenylpropylene was used in lieu of 3-(4-hydroxyphenyl)propylene.

As a result, the conversion of the starting material was 100%, the yield of the intermediate 1-phenyl-2,2-dimethoxypropane was 88%, and the yield of the desired phenylacetone was 87%.

Example 90

The reaction of Example 86 was repeated, except that n-butyl nitrite and n-butyl alcohol were used in lieu of methyl nitrite and methyl alcohol and the reaction temperature was changed to 60° C. and that the hydrolysis conditions were changed to 55° C. and 80 minutes.

As a result, the conversion of the starting material was 100%, the yield of the intermediate 1-(4-hydroxyphenyl)-2,2-di(n-butoxy) propane was 82%, and the yield of the desired 4-hydroxyphenylacetone was 80%.

Example 91

The reaction of Example 90 was repeated, except that 3-(4-methoxyphenyl) propylene was used in lieu of 3-(4-hydroxyphenyl) propylene.

As a result, the conversion of the starting material was 100%, the yield of the intermediate 1-(4-methoxyphenyl)-2,2-di(n-butoxy) propane was 89%, and the yield of the desired 4-methoxyphenylacetone was 87%.

Example 92

The reaction of Example 90 was repeated, except that 3-(4hydroxy-3-methoxyphenyl) propylene was used in lieu of 3-(4-hydroxyphenyl) propylene.

As a result, the conversion of the starting material was 100%, the yield of the intermediate 1-(4-hydroxy-3-methoxyphenyl)-2,2-di(n-butoxy) propane was 80%, and the yield of the desired 4-hydroxy-3-methoxyphenylacetone was 78%.

Example 93

The reaction of Example 90 was repeated, except that 3-(3,4-dimethoxyphenyl)propylene was used in lieu of 3-(4-hydroxyphenyl) propylene.

As a result, the conversion of the starting material was 100%, the yield of the intermediate 1-(3,4-dimethoxyphenyl)-2,2-di(n-butoxy) propane was 87%, and the yield of the desired 3,4-dimethoxyphenylacetone was 85%.

Example 94

The reaction of Example 86 was repeated, except that 3-(4-methoxyphenyl) propylene was used in lieu of 3-(4-hydroxyphenyl) propylene and the hydrolysis time was changed to 30 minutes.

As a result, the conversion of the starting material was 100%, the yield of the intermediate 1-(4-methoxyphenyl)-2,2-dimethoxypropane was 94%, and the yield of the desired 4-methoxyphenylacetone was 93%.

Example 95

The reaction of Example 94 was repeated, except that 3-(3,4-methylenedioxyphenyl) propylene was used in lieu of 3-(4-methoxyphenyl) propylene.

As a result, the conversion of the starting material was 100%, the yield of the intermediate 1-(3,4-methylenedioxyphenyl)-2,2-dimethoxypropane was 92%, and the yield of the desired 3,4-methylenedioxyphenylacetone was 91%.

Example 96

The reaction of Example 86 was repeated, except that 3-(4-hydroxy-3-methoxyphenyl) propylene was used in lieu of 3-(4-hydroxyphenyl) propylene, that n-propyl nitrite and n-propyl alcohol was used in lieu of methyl nitrite and methyl alcohol, and that the reaction temperature was changed to 30° C. and the hydrolysis was carried out at 50° C. for 60 minutes.

As a result, the conversion of the starting material was 100%, the yield of the intermediate 1-(4-hydroxy-3-methoxyphenyl)-2,2-di(n-propoxy) propane was 83%, and the yield of the desired 4-hydroxy-3-methoxyphenylacetone was 82%.

Example 97

The reaction of Example 86 was repeated, except that 3-(3,4-dimethoxyphenyl) propylene was used in lieu of 3-(4-hydroxyphenyl) propylene, ethyl nitrite and ethyl alcohol was used in lieu of methyl nitrite and methyl alcohol, and that the reaction temperature was charged to 30° C. and the hydrolysis was carried out at 50° C. for 60 minutes.

As a result, the conversion of the starting material was 100%, the yield of the intermediate 1-(3,4-dimethoxyphenyl)-2,2-diethoxypropane was 90%, and the yield of the desired 3,4-dimethoxyphenylacetone was 89%.

Example 98

The reaction of Example 86 was repeated, except that 3-(4-hydroxy-5-methoxy-3-nitrophenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4-hydroxy-5-methoxy-3-nitrophenyl)-2,2-dimethoxypropane was 83%, and the yield of the desired 4-hydroxy-5-methoxy-3-nitrophenylacetone was 81%.

Example 99

The reaction of Example 90 was repeated, except that 3-(4-hydroxy-5-methoxy-3-nitrophenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4-hydroxy-5-methoxy-3-nitrophenyl)-2,2-di(n-butoxy) propane was 78%, and the yield of the desired 4-hydroxy-5-methoxy-3-nitrophenylacetone was 75%.

Example 100

The reaction of Example 86 was repeated, except that 3-(4,5-dimethoxy-3-nitrophenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4,5-dimethoxy-3-nitrophenyl)-2,2-dimethoxypropane was 86%, and the yield of the desired 4,5-dimethoxy-3-nitrophenylacetone was 84%.

Example 101

The reaction of Example 90 was repeated, except that 3-(4,5-dimethoxy-3-nitrophenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4,5-dimethoxy-3-nitropheny)-2,2-di(n-butoxy) propane was 82%, and the yield of the desired 4,5-dimethoxy-3-nitrophenylacetone was 79%.

Example 102

The reaction of Example 90 was repeated, except that 3-(3-chloro-4-methoxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(3-chloro-4-methoxyphenyl)-2,2-di(n-butoxy) propane was 89%, and the yield of the desired 3-chloro-4-methoxyphenylacetone was 86%.

Example 103

The reaction of Example 86 was repeated, except that 3-(3-chloro-4-methoxyphenyl) propylene was used in lieu of 3-(4-hydroxyphenyl) propylene and that n-hexyl nitrite and n-hexyl alcohol were used in lieu of methyl nitrite and methyl alcohol and that the reaction temperature was changed to 60° C. and the hydrolysis was carried out at 50° C. for 60 minutes.

As a result, the conversion of the starting material was 100%, the yield of the intermediate 1-(3-chloro-4-methoxyphenyl)-2,2-di(n-hexyloxy) propane was 85%, and the yield of the desired 3-chloro-4-methoxyphenylacetone was 82%.

Example 104

The reaction of Example 86 was repeated, except that 3-(3-bromo-4-ethoxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(3-bromo-4-ethoxyphenyl)-2,2-dimethoxypropane was 90%, and the yield of the desired 3-bromo-4-ethoxyphenylacetone was 88%.

Example 105

The reaction of Example 86 was repeated, except that 3-(3-bromo-4-ethoxyphenyl) propylene, benzyl nitrite, and benzyl alcohol were used in lieu of 3-(4-hydroxyphenyl) propylene, methyl nitrite, and methyl alcohol, respectively and that the reaction temperature was 60° C. and the hydrolysis was carried out at 50° C. for 60 minutes.

As a result, the conversion of the starting material was 100%, the yield of the intermediate 1-(3-bromo-4-ethoxyphenyl)-2,2-di(benzyloxy)propane was 84%, and the yield of the desired 3-bromo-4-ethoxyphenylacetone was 81%.

Example 106

The reaction of Example 90 was repeated, except that 3-(4-methoxy-3-methylphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4-methoxy-3-methylphenyl)-2,2-di(n-butoxy) propane was 88%, and the yield of the desired 4-methoxy-3-methylphenylacetone was 86%.

Example 107

The reaction of Example 86 was repeated, except that 3-(4-methoxy-3-methylphenyl) propylene, n-pentyl nitrite, and n-pentyl alcohol were used in lieu of 3-(4-hydroxyphenyl) propylene, methyl nitrite, and methyl alcohol and that the reaction temperature was 60° C. and the hydrolysis was carried out at 50° C. for 60 minutes.

As a result, the conversion of the starting material was 100%, the yield of the intermediate 1-(4-methoxy-3-methylphenyl)-2,2-di(n-pentyloxy) propane was 86%, and the yield of the desired 4-methoxy-3-methylphenylacetone was 84%.

Example 108

The reaction of Example 90 was repeated, except that 3-phenylpropylene was used in lieu of 3-(4-hydroxyphenyl) propylene and that the hydrolysis was carried out at 50° C. for 60 minutes.

As a result, the conversion of the starting material was 100%, the yield of the intermediate 1-phenyl-2,2-di(n-butoxy) propane was 85%, and the yield of the desired phenylacetone was 83%.

Example 109

The reaction of Example 86 was repeated, except that 3-(3-amino-4-methoxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(3-amino-4-methoxyphenyl)-2,2-dimethoxypropane was 86%, and the yield of the desired 3-amino-4-methoxyphenylacetone was 84%.

Example 110

The reaction of Example 90 was repeated, except that 3-(3-amino-4-methoxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(3-amino-4-methoxyphenyl)-2,2-di(n-butoxy) propane was 81%, and the yield of the desired 3-amino-4-methoxyphenylacetone was 78%.

Example 111

The reaction of Example 86 was repeated, except that 3-(2-hydroxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(2-hydroxyphenyl)-2,2-dimethoxypropane was 86%, and the yield of the desired 2-hydroxyphenylacetone was 85%.

Example 112

The reaction of Example 86 was repeated, except that 3-(2-methoxyphenyl) propylene was used in lieu of 3-(4-hydroxyphenyl) propylene and that the hydrolysis was carrid out at 50° C. for 60 minutes.

As a result, the conversion of the starting material was 100%, the yield of the intermediate 1-(2-methoxyphenyl)-2,2-dimethoxypropane was 92%, and the yield of the desired 2-methoxyphenylacetone was 91%.

Example 113

The reaction of Example 86 was repeated, except that 3-(4-benzyloxy-3-methoxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4-benzyloxy-3-methoxyphenyl)-2,2-dimethoxypropane was 90%, and the yield of the desired 4-benzyloxy-3-methoxyphenylacetone was 88%.

Example 114

The reaction of Example 86 was repeated, except that 3-(4-methoxy-3-benzyloxyphenyl) propylene was used in lieu of 3-(4-hydroxyphenyl) propylene and that the hydrolysis was carried out at 50° C. for 60 minutes.

As a result, the conversion of the starting material was 100%, the yield of the intermediate 1-(4-methoxy-3-benzyloxyphenyl)-2,2-dimethoxypropane was 90%, and the yield of the desired 4-methoxy-3-benzyloxyphenylacetone was 88%.

Examples 115 to 118

A 0.10 mole amount of the starting 3-(4-hydroxy-3-methoxyphenyl propylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction mixture was hydrolyzed by adding 36 g of water at 50° C. for 60 minutes.

The catalyst used and results are shown in Table 13.

TABLE 13

| Example No. | Catalyst | Conversion of starting material | Yield of intermediate*1 | Yield of desired product*2 |
|---|---|---|---|---|
| 115 | palladium bromide | 100% | 84% | 82% |
| 116 | palladium acetate | 53% | 19% | 18% |
| 117 | palladium nitrate | 73% | 29% | 28% |
| 118 | palladium sulfate | 50% | 18% | 17% |

*1 1-(4-hydroxy-3-methoxyphenyl)-2,2-di(n-butoxy) propane
*2 4-hydroxy-3-methoxyphenylacetone

Examples 119 to 122

A 0.10 mole amount of the starting 3-(3,4-dimethoxyphenyl) propylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction mixture was hydrolyzed by adding 36 g of water at 55° C. for 80 minutes.

The catalysts used and results are shown in Table 14.

TABLE 14

| Example No. | Catalyst | Conversion of starting material | Yield of intermediate*1 | Yield of desired product*2 |
|---|---|---|---|---|
| 119 | palladium bromide | 100% | 90% | 88% |
| 120 | palladium acetate | 60% | 23% | 22% |
| 121 | palladium nitrate | 77% | 36% | 35% |
| 122 | palladium sulfate | 56% | 23% | 22% |

*1 1-(3,4-dimethoxyphenyl)-2,2-di(n-butoxy) propane
*2 3,4-dimethoxyphenylacetone

Examples 123 and 124

A 0.10 mole amount of the starting 3-(3-chloro-4-methoxyphenyl) propylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction mixture was hydrolyzed at 50° C. for 60 minutes by adding 36 g of water thereto.

The catalysts used and results are shown in Table 15.

TABLE 15

| Example No. | Catalyst | Conversion of starting material | Yield of intermediate*1 | Yield of desired product*2 |
|---|---|---|---|---|
| 123 | palladium bromide | 100% | 92% | 89% |
| 124 | palladium acetate | 62% | 28% | 27% |

*1 1-(3-chloro-4-methoxyphenyl)-2,2-di(n-butoxy) propane
*2 3-chloro-4-methoxyphenylacetone

Examples 125 and 126

A 0.10 mole amount of the starting 3-(4-ethoxy-2-methylphenyl) propylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction products were hydrolyzed at 50° C. for 60 minutes by adding 36 g of water thereto.

The catalysts used and the results are shown in Table 16.

TABLE 16

| Example No. | Catalyst | Conversion of starting material | Yield of intermediate*1 | Yield of desired product*2 |
|---|---|---|---|---|
| 125 | palladium bromide | 100% | 87% | 85% |
| 126 | palladium nitrate | 66% | 31% | 30% |

*1 1-(4-ethoxy-2-methylphenyl)-2,2-di(n-butoxy) propane
*2 4-ethoxy-2-methylphenylacetone

Examples 127 and 128

A 0.10 mole amount of the starting 3-(4,5-dimethoxy-3-nitrophenyl) propylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction mixture was hydrolyzed at 50° C. for 60 minutes by adding 36 g of water thereto.

The catalysts used and the results are shown in Table 17.

TABLE 17

| Example No. | Catalyst | Conversion of starting material | Yield of intermediate*1 | Yield of desired product*2 |
|---|---|---|---|---|
| 127 | palladium nitrate | 70% | 39% | 38% |

TABLE 17-continued

| Example No. | Catalyst | Conversion of starting material | Yield of intermediate*1 | Yield of desired product*2 |
|---|---|---|---|---|
| 128 | palladium sulfate | 58% | 27% | 26% |

*1 1-(4,5-dimethoxy-3-nitrophenyl)-2,2-di(n-butoxy) propane
*2 4,5-dimethoxy-3-nitrophenylacetone

Examples 129 and 130

A 0.10 mole amount of the starting 3-phenylpropylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction mixture was hydrolyzed at 50° C. for 60 minutes by adding 36 g of water thereto.

The catalysts used and the results are shown in Table 18.

TABLE 18

| Example No. | Catalyst | Conversion of starting material | Yield of intermediate*1 | Yield of desired product*2 |
|---|---|---|---|---|
| 129 | palladium bromide | 100% | 90% | 88% |
| 130 | palladium acetate | 56% | 22% | 21% |

*1 1-phenyl-2,2-di(n-butoxy) propane
*2 phenylacetone

Examples 131 and 132

A 0.10 mole amount of the starting 3-(3-amino-4-methoxyphenyl) propylene, 0.25 mole of n-butyl nitrite, 0.5 liter of n-butyl alcohol, and 0.006 mole of a catalyst were charged into a reaction vessel. The reaction was carried out at a temperature of 60° C. for 1.5 hours. Then, the reaction mixture was hydrolyzed at 50° C. for 60 minutes by adding 36 g of water thereto.

The catalysts used and the results are shown in Table 19.

TABLE 19

| Example No. | Catalyst | Conversion of starting material | Yield of intermediate*1 | Yield of desired product*2 |
|---|---|---|---|---|
| 131 | palladium bromide | 100% | 88% | 86% |
| 132 | palladium nitrate | 71% | 35% | 34% |

*1 1-(3-amino-4-methoxyphenyl)-2,2-di(n-butoxy) propane
*2 3-amino-4-methoxyphenylacetone

Example 133

A 0.10 mole amount of the starting 3-phenylpropylene, 0.25 mole of methyl nitrite, 0.5 liter of methyl alcohol, 0.00025 mole of trimethylamine, and 0.0005 mole of a palladium chloride catalyst were charged into a reaction vessel. Then, the reaction was carried out at a temperature of 20° C. for 1.5 hours.

After completion of the reaction, the reaction mixture was gas chromatographically analyzed to quantitatively determine the unreacted starting material and the resultant intermediate product (1-phenyl-2,2-dimethoxypropane). As a result, the conversion of the starting material was 95%, the yield of the intermediate product was 85% and the Pd turn-over number was 170.

The reaction mixture (containing the intermediate product) obtained above was hydrolyzed at a temperature of 50° C. for 60 minutes by adding 36 g of water thereto.

After the completion of the hydrolysis, the desired phenylacetone was quantitatively determined by a gas chromatographical analysis. The yield of the desired product was 84%.

Example 134

A 0.10 mole amount of the starting 3-(3,4-dimethoxyphenyl) propylene, 0.25 mole of methyl nitrite, 0.5 liter of methyl alcohol, 0.00025 mole of triethylamine, and 0.0005 mole of a palladium chloride catalyst were charged into a reaction vessel. The reaction was carried out at a temperature of 20° C. for 1.5 hours.

Then, the reaction mixture was hydrolyzed at 50° C. for 60 minutes by adding 36 g of water thereto.

The results are shown in Table 20.

Examples 135 to 143

Example 134 was repeated, except that various amines listed in Table 20 were used in lieu of triethylamine.

The results are shown in Table 20.

TABLE 20

| Example No. | Amines | Conversion*1 of starting material (%) | Yield of*2 intermediate (%) | Pd turn-over number | Yield*3 of desired product (%) |
|---|---|---|---|---|---|
| 134 | triethylamine | 97 | 91 | 182 | 90 |
| 135 | trimethylamine | 97 | 89 | 178 | 89 |
| 136 | tripropylamine | 96 | 89 | 178 | 88 |
| 137 | tributylamine | 93 | 84 | 168 | 83 |
| 138 | dimethylamine | 96 | 88 | 176 | 87 |
| 139 | diethylamine | 96 | 88 | 176 | 86 |
| 140 | dipropylamine | 96 | 87 | 174 | 86 |
| 141 | methylamine | 96 | 87 | 174 | 86 |
| 142 | ethylamine | 96 | 88 | 176 | 87 |
| 143 | propylamine | 95 | 85 | 170 | 83 |

*1 3-(3,4-dimethoxyphenyl) propylene
*2 1-(3,4-dimethoxyphenyl)-2,2-dimethoxypropane
*3 3,4-dimethoxyphenylacetone

Example 144

The reaction of Example 133 was repeated, except that 3-(4-hydroxy-3-methoxyphenyl)propylene was used in lieu of 3-phenylpropylene.

As a result, the conversion of the starting 3-(4-hydroxy-3-methoxyphenyl)propylene was 90%, the yield of the intermediate 1-(4-hydroxy-3-methoxyphenyl)-2,2-dimethyoxypropane was 78%, the Pd turn-over number was 156, and the yield of the desired 4-hydroxy-3-methoxyphenylacetone was 77%.

Example 145

The reaction of Example 133 was repeated, except that 3-(3,4-methylenedioxyphenyl)propylene was used in lieu of 3-phenylpropylene.

As a result, the conversion of the starting 3-(3,4-methylenedioxyphenyl)propylene was 95%, the yield of the intermediate 1-(3,4-methylenedioxyphenyl)-2,2-dimethoxypropane was 88%, the Pd turn-over number was 176, and the yield of the desired 3,4-methylenedioxyphenylacetone was 87%.

Examples 146 to 152

The reaction of Example 134 was repeated, except that each of various 3-phenylpropylenes listed in Table 21 was used in lieu of 3-(3,4-dimethoxyphenyl)propylene.

The results are shown in Table 21.

Examples 153 to 155

The reaction of Example 133 was repeated, except that 0.10 mole of each of various 3-phenylpropylenes listed in Table 22 and 0.00025 mole of each of various amines listed in Table 22 were used in lieu of those of Example 133 and that 0.0005 mole of palladium bromide was used in lieu of palladium chloride.

The results are shown in Table 22.

TABLE 22

| Example No. | Amines | Starting material Name | Conversion (%) | Intermediate Name | Yield (%) | Pd turn-over number | Desired product Name | Yield (%) |
|---|---|---|---|---|---|---|---|---|
| 153 | piperidine | 3-(3,4-dimethoxyphenyl) propylene | 99 | 1-(3,4-dimethoxyphenyl)-2,2-dimethoxypropane | 95 | 190 | 3,4-dimethoxyphenylacetone | 94 |
| 154 | N—methyl piperidine | 3-(3,4-methylenedioxyphenyl) propylene | 99 | 1-(3,4-methylenedioxyphenyl)-2,2-dimethoxypropane | 94 | 188 | 3,4-methylenedioxyphenylacetone | 92 |
| 155 | pyrrolidine | 3-(4-hydroxy-3-methoxyphenyl) propylene | 87 | 1-(4-hydroxy-3-methoxyphenyl)-2,2-dimethoxypropane | 87 | 172 | 4-hydroxy-3-methoxyphenylacetone | 86 |

Example 156 to 158

A 0.10 mole amount of each of the starting 3-phenylpropylene listed in Table 23, 0.25 mole of n-butyl nitrite, 0.5 liter of n-butyl alcohol, 0.00025 mole of triethylamine, and 0.0005 mole of a palladium chloride catalyst were charged into a reaction vessel. The reaction was carried out at a temperature of 60° C. for 1.5 hours. Then, the reaction mixture was hydrolyzed at a temperature of 50° C. for 60 minutes by adding 36 g of water thereto.

The results are shown in Table 23.

TABLE 21

| Example No. | Starting material Name | Conversion (%) | Intermediate Name | Yield (%) | Pd turn-over | Desired product Name | Yield (%) |
|---|---|---|---|---|---|---|---|
| 146 | 3-(4-hydroxyphenyl) propylene | 95 | 1-(4-hydroxyphenyl)-2,2-dimethoxy propane | 81 | 162 | 4-hydroxyphenylacetone | 80 |
| 147 | 3-(4-methoxyphenyl) propylene | 96 | 1-(4-methoxyphenyl)-2,2-dimethoxypropane | 87 | 174 | 4-methoxyphenylacetone | 87 |
| 148 | 3-(4-hydroxy-3-methoxyphenyl) propylene | 91 | 1-(4-hydroxy-3-methoxyphenyl)-2,2-dimethoxypropane | 79 | 158 | 4-hydroxy-3-methoxyphenylacetone | 79 |
| 149 | 3-(3,4-methylenedioxyphenyl) propylene | 96 | 1-(3,4-methylenedioxyphenyl)-2,2-dimethoxypropane | 90 | 180 | 3,4-methylenedioxyphenylacetone | 89 |
| 150 | 3-(3-benzyloxy-4-methoxyphenyl) propylene | 89 | 1-(3-benzyloxy-4-methoxyphenyl)-2,2-dimethoxypropane | 80 | 160 | 3-benzyloxy-4-methoxyphenylacetone | 79 |
| 151 | 3-(4-benzyloxy-3-methoxyphenyl) propylene | 87 | 1-(4-benzyloxy-3-methoxyphenyl)-2,2-dimethoxypropane | 76 | 152 | 4-benzyloxy-3-methoxyphenylacetone | 75 |
| 152 | 3-(4-ethylphenyl) propylene | 91 | 1-(4-ethylphenyl)-2,2-dimethoxypropane | 78 | 156 | 4-ethylphenylacetone | 77 |

TABLE 23

| Example No. | Starting material Name | Conversion (%) | Intermediate Name | Yield (%) | Pd turn-over number | Desired product Name | Yield (%) |
|---|---|---|---|---|---|---|---|
| 156 | 3-(3,4-methylenedioxyphenyl) | 62 | 1-(3,4-methylenedioxyphenyl)- | 56 | 112 | 3,4-methylenedioxyphenyl- | 54 |

TABLE 23-continued

| Example No. | Starting material | | Intermediate | | | Desired product | |
|---|---|---|---|---|---|---|---|
| | Name | Conversion (%) | Name | Yield (%) | Pd turn-over number | Name | Yield (%) |
| | propylene | | 2,2-di(n-butoxy)propane | | | acetone | |
| 157 | 3-(3,4-dimethoxy-3-methoxyphenyl)propylene | 71 | 1-(3,4-dimethoxyphenyl)-2,2-di(n-butoxy)propane | 63 | 126 | 3,4-dimethoxyphenylacetone | 61 |
| 158 | 3-(4-hydroxy-3-methoxyphenyl)propylene | 58 | 1-(4-hydroxy-3-methoxyphenyl)-2,2-di(n-butoxy)propane | 48 | 96 | 4-hydroxy-3-methoxyphenylacetone | 47 |

Example 159

A 0.10 mole amount of the starting 3-(3,4-dimethoxyphenyl)propylene, 0.25 mole of methyl nitrite, 0.5 liter of methyl alcohol, and 0.003 mole (corresponding to 0.006 mole of palladium atom) of the dimer of dichloroethylene palladium (II) as a catalyst were charged into a reaction vessel. Then, the reaction was carried out at a temperature of 20° C. for 1.5 hours.

After the completion of the reaction, the reaction mixture was gas chromatographically analyzed to quantitatively determine the unreacted starting material and the resultant intermediate 1-(3,4-dimethoxyphenyl)-2,2-dimethoxypropane. As a result, the conversion of the starting material was 100% and the yield of the intermediate product was 92%.

The reaction mixture (containing the intermediate product) obtained above was hydrolyzed at a temperature of 50° C. for 60 minutes by adding 36 g of water thereto.

After the completion of the hydrolysis, the desired 3,4-dimethoxyphenylacetone was quantitatively determined by a gas chromatographical analysis. The yield of the desired product was 91%.

Example 160

The reaction of Example 159 was repeated, except that 0.006 mole of bis(acetonitrile) palladium (II) chloride was used as a catalyst.

As a result, the conversion of the starting 3-(3,4-dimethoxyphenyl)propylene was 100%, the yield of the intermediate 1-(3,4-dimethoxyphenyl)-2,2-dimethoxypropane was 91%, and the yield of the desired 3,4-dimethoxyphenylacetone was 90%.

Example 161

The reaction of Example 159 was repeated, except that 0.10 mole of 3-(4-hydroxy-3-methoxyphenyl)propylene as a starting material and 0.006 mole of bis(acetonitrile) palladium (II) chloride as a catalyst were used.

As a result, the conversion of the starting material was 100%, the yield of the intermediate 1-(4-hydroxy-3-methoxyphenyl)-2,2-dimethoxypropane was 85%, and the yield of the desired 4-hydroxy-3-methoxyphenylacetone was 84%.

Example 162

The reaction of Example 159 was repeated, except that 0.10 mole of 3-(3,4-methylenedioxyphenyl)propylene as a starting material and 0.006 mole of bis(benzonitrile) palladium (II) chloride were used.

As a result, the conversion of the starting material was 100%, the yield of the intermediate 1-(3,4-methylenedioxyphenyl)-2,2-dimethoxypropane was 90%, and the yield of the desired 3,4-methylenedioxyphenylacetone was 89%.

Example 163

The reaction of Example 159 was repeated, except that 0.25 mole of n-butyl nitrite and 0.5 liter of n-butyl alcohol were used in lieu of methyl nitrite and methyl alcohol and that the reaction temperature was changed to 60° C.

As a result, the conversion of the starting material was 100%, the yield of the intermediate 1-(3,4-dimethoxyphenyl)-2,2-di(n-butoxy)propane was 86%, and the yield of the desired 3,4-dimethoxyphenylacetone was 85%.

Example 164

A 0.10 mole amount of the starting 3-phenylpropylene, 0.25 mole of methyl nitrite, 0.5 liter of methyl alcohol, 0.0005 mole of palladium chloride, and 0.0025 mole of cuprous chloride, were charged into a reaction vessel. Then, the reaction was carried out at a temperature of 20° C. for 1.5 hours.

After the completion of the reaction, the reaction mixture was gas chromatographically analyzed to quantitatively determine the unreacted starting material and the resultant intermediate 1-phenyl-2,2-dimethoxypropane. As a result, the conversion of the starting material was 96%, the yield of the intermediate product was 86%, and the Pd turn-over number was 172.

The reaction mixture (containing the intermediate product) obtained above was hydrolyzed at a temperature of 50° C. for 60 minutes by adding 36 g of water thereto.

After the completion of the hydrolysis, the desired phenylacetone was quantitatively determined by a gas chromatographical analysis. The yield of the desired product was 85%.

Examples 165 to 170

The reaction of Example 164 was repeated, except that 0.10 mole of each of 3-phenylpropylenes listed in Table 24 was used as a starting material and that 0.0025 mole of $CuCl_2$ or $CuCl$ was used as a copper compound.

The results are shown in Table 24.

TABLE 24

| Example No. | Starting material Name | Conversion (%) | Copper compound | Intermediate Name | Yield (%) | Pd turn-over number | Desired product Name | Yield (%) |
|---|---|---|---|---|---|---|---|---|
| 165 | 3-(4-hydroxy-3-methoxyphenyl) propylene | 93 | CuCl₂ | 3-(4-hydroxy-3-methoxyphenyl)-2,2-dimethoxypropane | 83 | 166 | 4-hydroxy-3-methoxyphenyl-acetone | 82 |
| 166 | | 94 | CuCl | | 85 | 170 | | 84 |
| 167 | 3-(3,4-dimethoxyphenyl) propylene | 98 | CuCl₂ | 1-(3,4-dimethoxyphenyl)-2,2-dimethoxypropane | 89 | 178 | 3,4-dimethoxyphenylacetone | 88 |
| 168 | | 97 | CuCl | | 89 | 178 | | 88 |
| 169 | 3-(3,4-methylenedioxyphenyl) propylene | 96 | CuCl₂ | 1-(3,4-methylenedioxyphenyl)-2,2-dimethoxypropane | 90 | 180 | 3,4-methylenedioxyphenyl-acetone | 90 |
| 170 | | 96 | CuCl | | 89 | 178 | | 87 |

Example 171 to 173

A 0.10 mole amount of the starting 3-phenylpropylene, listed in Table 25, 0.25 mole of n-butyl nitrite, 0.5 liter of n-butyl alcohol, 0.0025 mole of CuCl₂ as a copper compound, and 0.0005 mole of a palladium chloride catalyst were charged into a reaction vessel. The reaction was carried out at a temperature of 60° C. for 1.5 hours.

After completion of the reaction, the reaction mixture was treated in the same manner as in Example 159. The results are shown in Table 25.

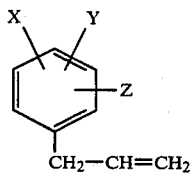

(II)

wherein X, Y, and Z are as defined above, with an alkyl nitrite having the general formula (III):

TABLE 25

| Example No. | Starting material Name | Conversion (%) | Intermediate Name | Yield (%) | Pd turn-over number | Desired product Name | Yield (%) |
|---|---|---|---|---|---|---|---|
| 171 | 3-(4-hydroxy-3-methoxyphenyl) propylene | 62 | 1-(4-hydroxy-3-methoxyphenyl)-2,2-di(n-butoxy)propane | 53 | 106 | 4-hydroxy-3-methoxyphenyl-acetone | 51 |
| 172 | 3-(3,4-dimethoxyphenyl) propylene | 73 | 1-(3,4-dimethoxyphenyl)-2,2-di(n-butoxy)propane | 65 | 130 | 3,4-dimethoxyphenylacetone | 63 |
| 173 | 3-(3,4-methylenedioxyphenyl) propylene | 67 | 1-(3,4-methylenedioxyphenyl)-2,2-di(n-butoxy)propane | 60 | 120 | 3,4-methylenedioxyphenyl-acetone | 61 |

We claim:

1. A process for producing a phenylacetone or its derivative having the general formula (I):

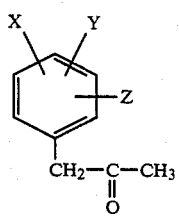

(I)

wherein X, Y, and Z are independently a hydrogen atom, a hydroxyl group, a halogen atom, a nitro group, an amino group, a lower alkyl group having 1 to 6 carbon atoms, a lower alkoxy group having 1 to 6 carbon atoms, or a benzyloxy group, and any two substituents of X, Y, and Z may form, together with the benzene ring, a heterocyclic ring having 5 to 7 members including 1 or 2 oxygen atoms comprising the step of reacting a 3-phenylpropylene or its derivative having the general formula (II):

RONO (III)

wherein R is an aliphatic, aromatic, or alicyclic saturated or unsaturated hydrocarbon group in the presence of (a) water, (b) an alcohol, and (c) a palladium catalyst.

2. A process as claimed in claim 1, wherein said palladium catalyst is a palladium salt.

3. A process as claimed in claim 1, wherein said palladium catalyst is a palladium complex.

4. A process as claimed in claim 1, wherein the alkyl group of the alcohol is the same as that of the alkyl nitrite.

5. A process as claimed in claim 1, wherein said reaction is carried out at a temperature of 0° C. to 150° C.

6. A process as claimed in claim 1, wherein said reaction is carried out further in the presence of (d) an amine.

7. A process as claimed in claim 6, wherein said amine has the general formula (V):

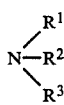

(V)

wherein $R^1$, $R^2$, and $R^3$ are the same or different and represent a hydrogen atom and a lower alkyl group having 1 to 6 carbon atoms and two groups of $R^1$, $R^2$, and $R^3$ are alkylene groups and may combine to form a ring.

8. A process as claimed in claim 1, wherein said reaction is carried out further in the presence of (e) a copper compound.

9. A process for producing a phenylacetone or its derivative having the general formula (I):

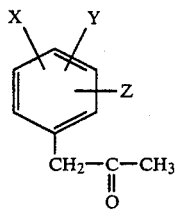 (I)

wherein X, Y, and Z are independently a hydrogen atom, a hydroxyl group, a halogen atom, a nitro group, an amino group, a lower alkyl group having 1 to 6 carbon atoms, a lower alkoxy group having 1 to 6 carbon atoms, or a benzyloxy group, and any two substituents of X, Y, and Z may form, together with the benzene ring, a heterocyclic ring having 5 to 7 members including 1 or 2 oxygen atoms comprising the step of reacting a 3-phenylpropylene or its derivative having the general formula (II):

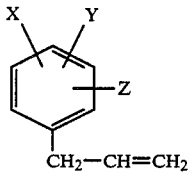 (II)

wherein X, Y, and Z are as defined above, with an alkyl nitrite having the general formula (III):

RONO            (III)

wherein R is an aliphatic, aromatic, or alicyclic saturated or unsaturated hydrocarbon group in the presence of (a) an alcohol and (b) a palladium catalyst to form 1-phenyl-2,2-dialkoxypropane or its derivative having the general formula (IV):

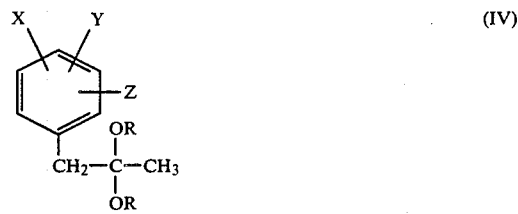 (IV)

wherein X, Y, Z and R are as defined above and, then, hydrolyzing the reaction product.

10. A process as claimed in claim 9, wherein said palladium catalyst is a palladium salt.

11. A process as claimed in claim 9, wherein said palladium catalyst is a palladium complex.

12. A process as claimed in claim 9, wherein the alkyl group of the alcohol is the same as that of the alkyl nitrite.

13. A process as claimed in claim 9, wherein said reaction is carried out at a temperature of 0° C. to 150° C.

14. A process as claimed in claim 9, wherein said reaction is carried out further in the presence of (c) an amine.

15. A process as claimed in claim 14, wherein said amine has the general formula (V):

 (V)

wherein $R^1$, $R^2$, and $R^3$ are the same or different and represent a hydrogen atom and a lower alkyl group having 1 to 6 carbon atoms and two groups of $R^1$, $R^2$, and $R^3$ are alkylene groups and may combine to form a ring.

16. A process as claimed in claim 9, wherein said reaction is carried out further in the presence of (d) a copper compound.

* * * * *